United States Patent [19]

Gardner

[11] 4,165,742
[45] Aug. 28, 1979

[54] SYRINGE CONNECTABLE TO A WATER FAUCET

[76] Inventor: Ina F. Gardner, Rte. 1, Box 445, Overton, Tex. 75684

[21] Appl. No.: 791,195

[22] Filed: Apr. 27, 1977

[51] Int. Cl.² ............................................. A61M 3/00
[52] U.S. Cl. ............................................. 128/229
[58] Field of Search ....................... 128/229, 224, 239

[56] References Cited

U.S. PATENT DOCUMENTS

| | | | |
|---|---|---|---|
| 926,197 | 6/1909 | Kim | 128/229 |
| 1,203,803 | 11/1916 | Speers | 128/229 |
| 1,655,664 | 1/1928 | Russell | 128/229 |
| 1,844,265 | 2/1932 | Smith | 128/229 |
| 1,861,932 | 6/1932 | Moore | 128/229 |
| 2,525,419 | 10/1950 | Mellinger et al. | 128/229 |
| 2,538,215 | 1/1951 | Stack | 128/229 |
| 3,142,297 | 7/1964 | Attebery | 128/229 |

*Primary Examiner*—John D. Yasko
*Attorney, Agent, or Firm*—Daniel Jay Tick

[57] ABSTRACT

A tube is removably coupled at a first end to a water faucet and has a syringe at its second opposite end. A slit is formed in the tube. A tubular branch extends from the tube around the slit for accommodating a capsule of medicament fittable through the slit into the tube. A cap removably covers the tubular branch. A clamp is removably and adjustably positioned on the tube intermediate the ends thereof for selectively preventing the flow of water through the tube.

1 Claim, 3 Drawing Figures

SYRINGE CONNECTABLE TO A WATER FAUCET

BACKGROUND OF THE INVENTION

The present invention relates to a syringe connectible to a water faucet.

BRIEF DESCRIPTION OF THE DRAWINGS

In order that the invention may be readily carried into effect, it will now be described with reference to the accompanying drawings, wherein.

DETAILED DESCRIPTION OF THE INVENTION

The syringe of the invention is connectible to a water faucet and comprises a tube 10 having spaced opposite first and second ends, shown in the FIGS. as the upper and lower ends, respectively.

Figure 1:
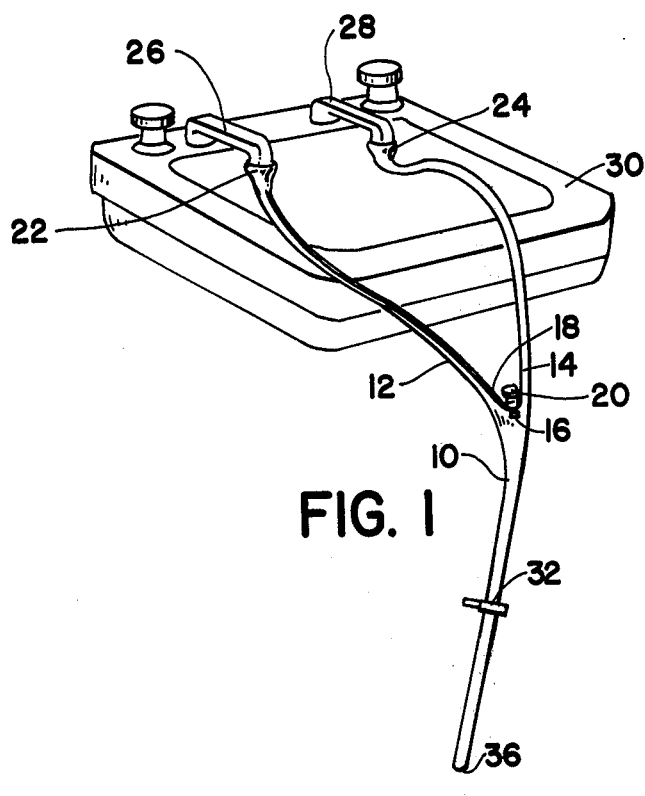
FIG. 1 is a perspective view of an embodiment of the syringe of the invention, coupled to a pair of water faucets.
Figure 2:
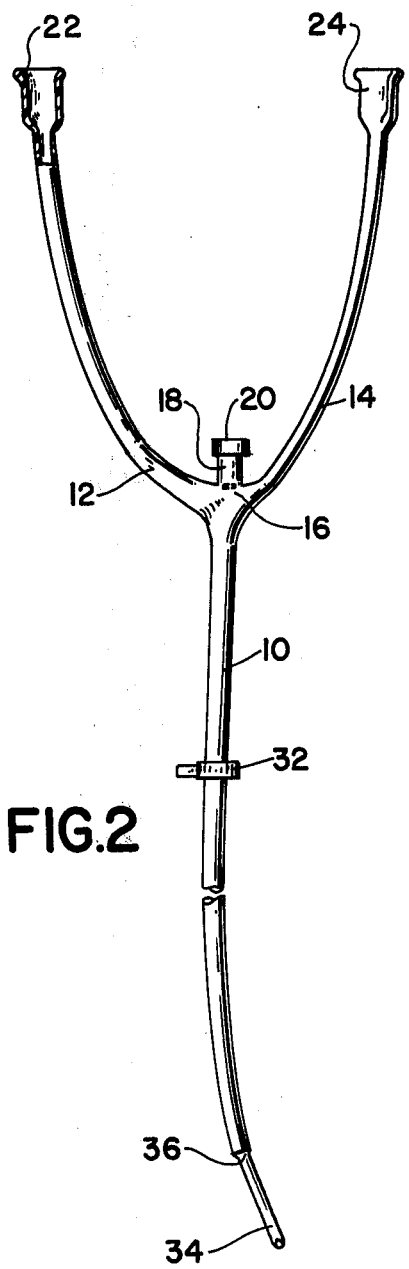
FIG. 2 is a view, on an enlarged scale, partly cut away and partly in section, of the embodiment of FIG. 1.

A connecting device at the first end of the tube 10 removably couples said tube to a water faucet 26 and/or 28. In the embodiment of FIGS. 1 and 2, the connecting device comprises a bifurcated first end of the tube 10 having a pair of connector tubes 12 and 14 extending from the first end of the tube. Each of the connector tubes 12 and 14 has a free end. An elastic bell-like coupling member 22 is provided at the free end of the connector tube 12 (FIGS. 1 and 2) and is removably positionable around the open end of the water faucet 26, as shown in FIG. 1. An elastic bell-like coupling member 24 is provided at the free end of the connector tube 14 (FIGS. 1 and 2) and is removably positionable around the open end of the water faucet 28, as shown in FIG. 1.

Figure 3:
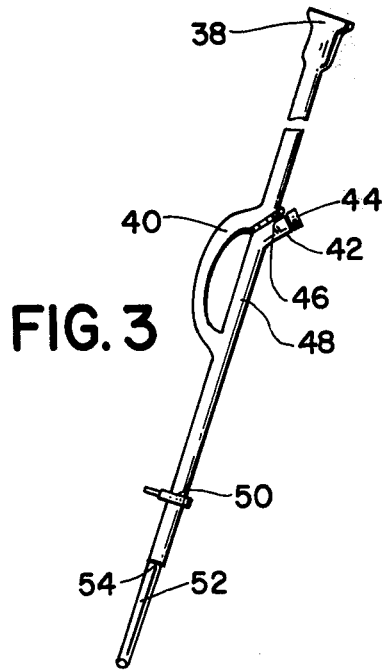
FIG. 3 is a view, on an enlarged scale, of another embodiment of the syringe of the invention.

In the embodiment of FIG. 3, the connecting device comprises an elastic bell-like coupling member 38 at the first end of the tube 10 removably positionable around the open end of a single water faucet.

A syringe tip 34 is removably coupled to the tube 10 at the second end 36 thereof, as shown in FIG. 2, in the embodiment of FIGS. 1 and 2. In the embodiment of FIG. 3, a syringe tip 52 is removably coupled to the tube 10 at the second end 54 thereof.

In the embodiment of FIGS. 1 and 2, a clamp 32 is removably and adjustably positioned on the tube 10 intermediate the first end and the second end 36 for selectively preventing a flow of water through said tube. In the embodiment of FIG. 3, a clamp 50 is removably and adjustably positioned on the tube 10 intermediate the first end and the second end 54 for selectively preventing a flow of water through said tube.

A medicament device is provided for inserting a medicament or medicinal preparation, solution, or the like, into the tube 10. The medicament device comprises a slit formed in the tube 10 at a point between the first end of the tube and the clamp 32 in the embodiment of FIGS. 1 and 2 and between the first end of the tube and the clamp 50 in the embodiment of FIG. 3. In the embodiment of FIGS. 1 and 2, a slit 16 is formed at the first end of the tube 10 in the area from which the connector tubes 12 and 14 extend. A tubular branch 18 extends from the tube 10 around the slit 16, as shown in FIGS. 1 and 2, for accommodating a capsule of medicament, medicine, medicinal preparation, chemical, or the like, fittable through said slit into said tube. A cap 20 removably covers the tubular branch 18 (FIGS. 1 and 2).

In the embodiment of FIG. 3, a slit 46 is formed in the tube 10 at a point between the first end of the tube and the clamp 50, as hereinbefore mentioned. A bypass tube 40 bridges the point of the tube 10 having the slit 46 formed therein, thereby bridging a section 48 of said tube (FIG. 3). The bypass tube 40 has spaced opposite ends opening from the tube 10 on both sides of the slit 46. A tubular branch 42 extends from the tube 10 around the slit 46, as shown in FIG. 3, for accommodating a capsule of medicament, medicine, medicinal preparation, chemical, or the like, fittable through said slit into said tube. A cap 44 removably covers the tubular branch 42 (FIG. 3).

An additional clamp 49 is adjustably positioned on the tube 10 intermediate the tubular branch 42 and the end of the bypass tube 40 closer to the first end of said tube, in the embodiment of FIG. 3. The clamp 49 selectively prevents a flow of water past the slit 46 in the tube 10 of FIG. 3.

When the water supplied via the faucets 26 and 28 has been adjusted as desired with regard to temperature and pressure, the clamp 32 is tightened. The usual syringe tip 34 may then be utilized in the usual manner by the user by insertion into a desired body orifice. Thus, if a douche is provided, for example, a douching preparation or chemicals are inserted into the tube 10 via the slit 16 or 46. The tube 10 is suitably long and the clamp 32 or 50 is suitably positioned for comfortable use.

Having described a preferred embodiment of my invention, it is understood that various changes can be made without departing from the spirit of my invention, and, I desire to cover by the appended claims all such modifications as fall within the true spirit and scope of my invention.

What I claim and seek to secure by Letters Patent is:

1. A syringe connectable to a water faucet, said syringe comprising a tube having spaced opposite first and second ends;

connecting means at the first end of the tube for removably coupling said tube to a water faucet;

a syringe tip removably coupled to said tube at the second end thereof;

clamping means removably and adjustably positioned on said tube intermediate the first and second ends thereof for selectively preventing a flow of water through said tube; and medicament means for inserting a medicament into said tube, said medicament means comprising a slit formed in said tube at a point between said first end of said tube and said clamping means, a tubular branch extending from said tube around said slit for accommodating a capsule of medicament fittable through said slit into said tube, and a cap removably covering the tubular branch, said connecting means comprising an elastic bell-like coupling member at the first end of said tube removably positionable around the open end of a water faucet, a bypass tube bridging the point of the tube having the slit formed therein and having spaced opposite ends opening from said tube on both sides of said slit, and additional clamping means adjustably positioned on said tube intermediate said tubular branch and the end of said bypass tube closer to said first end of said tube for selectively preventing a flow of water past said slit in said tube.

* * * * *